(12) United States Patent
Sieckmann et al.

(10) Patent No.: US 10,481,374 B2
(45) Date of Patent: *Nov. 19, 2019

(54) METHOD AND MICROSCOPY SYSTEM FOR SCANNING A SAMPLE

(71) Applicants: LEICA MICROSYSTEMS CMS GMBH, Wetzlar (DE); EMBL European Molecular Biology Laboratory, Heidelberg (DE)

(72) Inventors: Frank Sieckmann, Bochum (DE); Urban Liebel, Dielheim-Horrenberg (DE)

(73) Assignees: LEICA MICROSYSTEMS CMS GMBH, Wetzlar (DE); EMBL EUROPEAN MOLECULAR BIOLOGY LABORATORY, Heidelberg (DE)

( * ) Notice: Subject to any disclaimer, the term of this patent is extended or adjusted under 35 U.S.C. 154(b) by 275 days.

This patent is subject to a terminal disclaimer.

(21) Appl. No.: 15/426,118

(22) Filed: Feb. 7, 2017

(65) Prior Publication Data

US 2017/0146782 A1    May 25, 2017

Related U.S. Application Data

(63) Continuation of application No. 12/439,597, filed as application No. PCT/EP2007/059351 on Sep. 6, 2007, now Pat. No. 9,588,329.

(30) Foreign Application Priority Data

Sep. 6, 2006 (DE) .................. 10 2006 042 157

(51) Int. Cl.
*G02B 21/00* (2006.01)
*G01N 15/14* (2006.01)
(Continued)

(52) U.S. Cl.
CPC ..... *G02B 21/0084* (2013.01); *G01N 15/1475* (2013.01); *G02B 21/367* (2013.01);
(Continued)

(58) Field of Classification Search
CPC .............. G02B 21/0084; G02B 21/367; G06K 9/00147; G06K 9/00134; G01N 15/1475; G06F 19/3418
See application file for complete search history.

(56) References Cited

U.S. PATENT DOCUMENTS 5,257,182 A    10/1993    Luck et al.
5,793,969 A    8/1998    Kamentsky et al.
(Continued)

FOREIGN PATENT DOCUMENTS

DE    10222779 A1    3/2004
DE    10332060 A1    2/2005
(Continued)

OTHER PUBLICATIONS

U.S. Appl. No. 16/352,875, filed Mar. 14, 2019.
(Continued)

*Primary Examiner* — James M Pontius
(74) *Attorney, Agent, or Firm* — Leydig, Voit & Mayer, Ltd.

(57) ABSTRACT

A method for scanning a sample using an electrically or electronically controllable microscope includes performing a continuous scanning of the sample so as to repeatedly generate a plurality of images of the sample, each of the plurality of images corresponding to a different time, the microscope being controlled via a control computer during the scanning. The plurality of images are analyzed using at least one second computer connected via a network, wherein the at least one second computer is configured to classify each of the plurality of images as one of interesting and (Continued)

non-interesting while the continuous scanning of the sample with the microscope continues. The continuous scanning of the sample is automatically influenced based on the classifying of the images performed by the at least one second computer.

26 Claims, 7 Drawing Sheets

(51) Int. Cl.
  *G02B 21/36* (2006.01)
  *G06K 9/00* (2006.01)
  *G06F 19/00* (2018.01)
(52) U.S. Cl.
  CPC ..... *G06K 9/00134* (2013.01); *G06K 9/00147* (2013.01); *G06F 19/3418* (2013.01)

(56) References Cited

U.S. PATENT DOCUMENTS

| | | | |
|---|---|---|---|
| 5,836,877 A | 11/1998 | Zavislan | |
| 5,928,344 A | 7/1999 | Stierli | |
| 6,115,480 A | 9/2000 | Washizawa | |
| 6,259,807 B1 | 7/2001 | Ravkin | |
| 6,388,788 B1* | 5/2002 | Harris | G02B 21/0028 250/234 |
| 6,631,203 B2 | 10/2003 | Ellis et al. | |
| 6,684,092 B2 | 1/2004 | McClure | |
| 7,027,628 B1 | 4/2006 | Gagnon et al. | |
| 7,257,268 B2* | 8/2007 | Eichhorn | G06K 9/00147 375/E7.201 |
| 7,653,260 B2* | 1/2010 | Perz | G02B 21/365 382/128 |
| 7,870,284 B2 | 1/2011 | Hunt et al. | |
| 8,369,591 B2* | 2/2013 | Perz | G06T 7/11 382/128 |
| 9,588,329 B2* | 3/2017 | Sieckmann | G02B 21/367 |
| 2001/0050999 A1 | 12/2001 | Bacus et al. | |
| 2002/0015516 A1 | 2/2002 | Ruehl | |
| 2002/0124236 A1 | 9/2002 | Ruths et al. | |
| 2003/0036855 A1* | 2/2003 | Harris | G02B 21/0028 702/19 |
| 2003/0210262 A1 | 11/2003 | Gahm et al. | |
| 2003/0229299 A1* | 12/2003 | Shimura | G06T 7/0012 600/595 |
| 2004/0202357 A1* | 10/2004 | Perz | G06K 9/0014 382/128 |
| 2004/0236773 A1 | 11/2004 | Bacus et al. | |
| 2005/0058372 A1 | 3/2005 | Engelmann et al. | |
| 2005/0179892 A1 | 8/2005 | Gerstner et al. | |
| 2005/0254696 A1 | 11/2005 | Bacus et al. | |
| 2006/0007533 A1 | 1/2006 | Eichhorn et al. | |
| 2006/0045505 A1 | 3/2006 | Zeineh et al. | |
| 2006/0133657 A1 | 6/2006 | Schmid et al. | |
| 2006/0140472 A1 | 6/2006 | Shimoda et al. | |
| 2006/0278826 A1 | 12/2006 | Roberts et al. | |
| 2007/0031043 A1 | 2/2007 | Perz et al. | |
| 2007/0172100 A1 | 7/2007 | Lefebvre | |
| 2009/0069680 A1* | 3/2009 | Abe | A61B 8/08 600/440 |
| 2012/0113242 A1 | 5/2012 | Crandall et al. | |
| 2013/0322735 A1* | 12/2013 | Tamura | G06T 7/0004 382/144 |
| 2017/0011255 A1* | 1/2017 | Kaditz | G01R 33/48 |

FOREIGN PATENT DOCUMENTS

| | | |
|---|---|---|
| JP | 2001519944 A | 10/2001 |
| JP | 2004514920 A | 5/2004 |
| JP | 2005530225 A | 10/2005 |
| WO | WO 1992004620 A2 | 3/1992 |
| WO | WO 0184209 A | 11/2001 |
| WO | WO 2002066961 A1 | 8/2002 |
| WO | WO 2005119575 A2 | 12/2005 |
| WO | WO 2006023443 A | 3/2006 |

OTHER PUBLICATIONS

U.S. Appl. No. 12/439,597, filed Dec. 7, 2009.
International Search Report of PCT/EP2007/059351, dated Nov. 6, 2007, pp. 1-3.
"A grid-based image archival and analysis system", from S. Hastings et al., J. Am. Med. Inform assoc. 2005; 12: 286-295, published on May 1, 2005.
"Automated molecular microscopy: The new Leginon system" from C. Suloway et al., Journal of Structural Biology 151 (2005) 41-60, published on Apr. 19, 2005.

* cited by examiner

METHOD AND MICROSCOPY SYSTEM FOR SCANNING A SAMPLE

CROSS-REFERENCE TO PRIOR APPLICATIONS

This application is a continuation of U.S. application Ser. No. 12/439,597 which is a U.S. National Phase application under 35 U.S.C. § 371 of International Application No. PCT/EP2007/059351, filed Sep. 6, 2007, and claims benefit to German Patent Application No. 10 2006 042 157.4, filed Sep. 6, 2006, all of which applications are hereby incorporated by reference herein. The International Application was published in German on Mar. 13, 2008 as WO 2008/028944 under PCT Article 21(2).

FIELD

The present invention relates to a method and system for scanning a sample by means of an electrically and/or electronically controllable microscope, a plurality of images, in particular digital images, being generated at different locations in the sample and/or at different times, and the microscope being controlled by a control computer during a scanning operation.

BACKGROUND

The need to investigate biological samples in detail often exists in the life sciences sector. This applies especially to a wide variety of issues in biology, genetics, pharmacology, and the like. Cell division processes, for example, or the effect of a medication on cell development, can be investigated. In such investigations, the sample is typically observed and analyzed by means of a microscope.

Investigations using microscopes are preferable in other fields as well. In forensics, for example, one task is to discover, from a plurality of fibers, one deriving from a perpetrator. Further application areas encompass metallography, quality assurance, microtiter plate analysis, or pathology. All these application areas have in common the fact that a sample is preferably imaged or examined over a large region.

In this context, the microscope stage is often moved beneath the objective, or at least parts of the microscope are moved, and the sample is thereby scanned in linear or meander fashion or along another geometric trajectory. The movement of the microscope stage or of the moving part of the microscope is usually controlled electrically or electronically with the use of a control computer. The data obtained during the scanning operation are then stored on the control computer, and are made available to a user for later evaluation. The data acquired in this fashion are usually stored in a database.

With statistical investigations in particular, for example when investigating cell division, a very large quantity of data is preferably generated in order to discover a sufficient number of interesting cells. Only in this way is it possible to make sufficiently accurate statements about sample behavior in general. This involves repeatedly scanning the sample field by field along a geometric trajectory. If the number of individual fields is large, the problem exists that rapidly occurring processes can no longer be imaged with sufficient time resolution. The time span until a field is scanned again is relatively long. Processes that occur comparatively rapidly, for example in the context of cell division in biology, or fracture behavior or oxidation in metallography, therefore can no longer be observed with sufficient accuracy.

The time span between two scans of a field can be reduced by elevating the scanning rate, i.e. shortening the time required for each field; but other problems then occur. The movement of the specimen slide or of the moving part of the microscope is preferably more greatly accelerated and decelerated. A sufficient waiting time is therefore necessary to allow vibrations to decay. A steady sample is important for three-dimensional images. Tight limits are therefore placed on the speed of movement, and an upper boundary on the scanning rate exists. Individual sequences that can be assembled into a smooth movie are almost impossible in this context.

Complex regulation systems are typically used in order to image a specimen at relatively high speed and with high precision. Regulation systems of this kind, in which an electrically or electronically controllable microscope is connected to a control computer, are generally used. This control computer ensures maximally optimum movement and precise positioning of the sample. The problem still remains, however, that with mass scanning in particular, very large data quantities occur which is preferably appropriately stored. Data quantities on the order of several terabytes (TB) can quickly build up. For example, if cell division is to be observed over a period of 48 hours in an investigation of a microtiter plate having 384 scanning fields, considerable quantities of data are produced. Scanners in use at present supply images 8000×8000 pixels in size. In addition, three-dimensional data having 20 to 50 section planes are generated, and the sample is furthermore illuminated with different wavelengths. A simple calculation shows that the data quantity has already grown into the double-digit TB range. This data quantity must be not only appropriately stored, but also processed and evaluated during subsequent analysis.

SUMMARY

In an embodiment, the present invention provides a method for scanning a sample using an electrically or electronically controllable microscope. The method includes the steps of:

scanning the sample so as to generate a plurality of images of the sample, each of the plurality of images corresponding to at least one of a different region of the sample and a different time, the microscope being controlled via a control computer during the scanning;

analyzing the plurality of images using at least one second computer connected via a network; and at least one of classifying the plurality of images and influencing the scanning based on the analyzing.

BRIEF DESCRIPTION OF THE DRAWINGS

There are various ways of advantageously embodying and refining the teaching of the present invention. In conjunction with the explanation of the exemplifying embodiments of the present invention with reference to the drawings, an explanation will also be given of generally preferred embodiments and further developments of the teaching. In the drawings.

DETAILED DESCRIPTION

Figure 1:
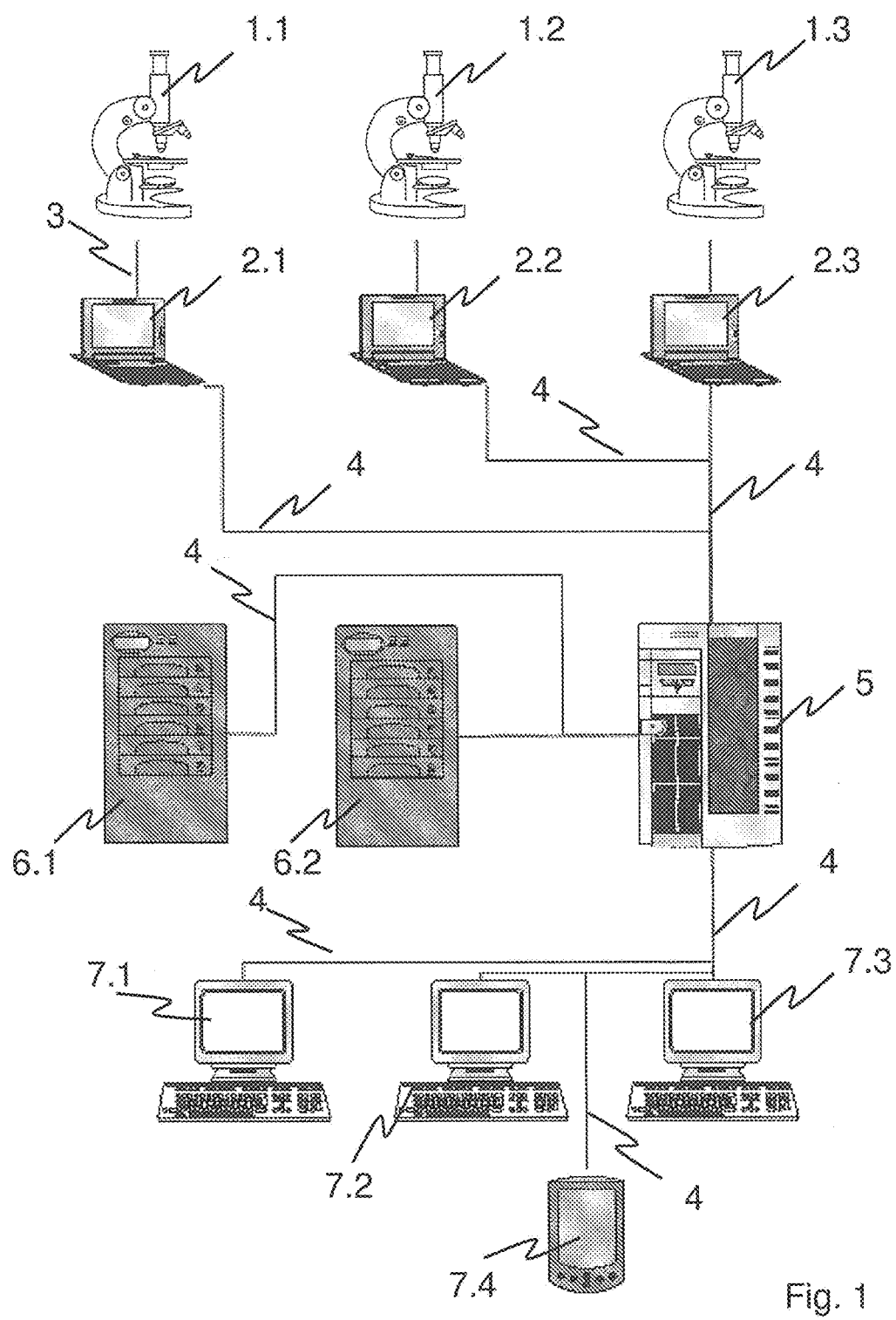
FIG. 1 schematically depicts a microscopy system according to an embodiment of the present invention having three microscopes.

An aspect of the present invention provides a method of scanning a sample by means of a microscope, even in a context in which a plurality of images are generated, that can be achieved quickly, precisely, and with a relatively small data volume.

The invention also relates to a microscopy system for scanning a sample by means of a microscope, the microscope or at least a part of the microscope being electrically and/or electronically controllable, and a plurality of images being generatable in a scanning operation at different locations in the sample and/or at different times.

In accordance therewith, the method in question for scanning a sample is further developed in such a way that an observation and/or analysis of the generated images is carried out in the context of at least one further computer connected via a network; and that based on its results, a classification of the images is performed and/or the scanning operation is influenced.

A microscopy system is configured in such a way that in addition to a control computer controlling the microscope, further computers are integratable into the system; and at least one of the further computers is configured to supervise the scanning operation and/or to observe and/or analyze the generated images.

In the context of a mass scan, only a fraction of the data obtained is interesting. A sample thus often needs to be investigated only with regard to particular events or properties, for example with regard to a cell division that is taking place, a hairline crack that is forming, or a particular configuration of a fiber in a fiber mixture. Regions that do not change or do not exhibit a desired property are generally uninteresting. It is these very regions, however, that are considerably more numerous than the interesting regions. The quantity of data generated can be effectively reduced if only a certain portion of the sample is imaged in detail. For that purpose, the sample is imaged only selectively.

Selective imaging of a sample typically requires, however, that an evaluation of the data obtained be carried out simultaneously, or at least close to simultaneously, with the scanning operation. A decision can thereby be made as to which data are required and which regions are to be scanned in more detail. The computing capacity of the control computer is usually not sufficient for concurrent data analysis. If the capacity does exist, there is a risk that interruptions in the control process will be caused by preemption in the computer's operating system, thus disrupting the scanning operation.

Classification of the images can be effectively achieved by "outsourcing" the observation and/or analysis of the generated data. A network-connected computer can be used for this purpose. A large number of computers that can be interconnected via a network are often present in research institutions. These computers are, for example, not used at night, and their capacity often is not completely utilized during the day. They can be combined via the network into a virtual system, and thereby used particularly effectively. In particular, parallel processing of data in mutually independent fashion is thereby achievable. The scanning operation and the observation and/or analysis of the images generated by the microscope can thus be performed substantially simultaneously or at least in close to real time. It thereby becomes possible to influence the scanning operation on the basis of the results from observation and/or analysis of the scanning operation. The invention thus makes possible "intelligent" microscopy.

Advantageously, observation and analysis of the sample can yield a classification into interesting and uninteresting regions. The classification can be accomplished by allocating specific geometric properties to the interesting objects in a sample, for example the cells that are dividing or a microcrack that is forming. A classifier looks for those properties and thus recognizes interesting regions. A rare event in the sample can thereby be effectively discovered.

If, in addition to rare events, unexpected events are also to be investigated, a classifier that investigates the sample in terms of standard properties could additionally be provided. For example, "normal" cells in a cell sample exhibit a certain structure. If objects are found in the sample that do not conform to those standard properties, then an unexpected event possibly exists. If an object cannot be classified as an interesting or uninteresting object, this indicates a candidate for an unexpected event. Because errors in image generation can of course also make classification impossible, a classification by, for example, an operator is necessary. Such candidates could therefore be presented to an operator so that he or she can perform a conclusive evaluation of the regions. Alternatively or additionally, further classifiers could filter further uninteresting regions out of the candidates for unexpected events.

To reduce complexity, provision could be made that the sample is first scanned at a comparatively low resolution. It is thereby possible, in simple fashion, to keep the quantity of data to be analyzed at a low level. The low-resolution data would then be conveyed to one or more of the further computers so that they can carry out an analysis of the images. The scanning operation can advantageously be continued during analysis. As a result, evaluation of the images occurs with a time offset with respect to acquisition of the images. The offset can, however, be kept relatively small by using computers connected via a network. The result is that the evaluation supplies a classification of the images generated by the microscope.

If an interesting region is identified in the images, that region could be imaged again at higher resolution. For that, the microscope stage or the movable part of the microscope would be moved in such a way that the interesting region can be imaged. In addition, an objective change could occur and/or automatic focusing could be carried out. If a comparatively rapid process is taking place in the interesting region, or if desired, that region could be investigated continuously for a certain time. The normal scanning operation would thereby be interrupted for a certain period of time. The sample could be both imaged in one scan layer and switched between multiple scan layers. In the latter case it would be possible to obtain data that permit a reconstruction of three-dimensional images. The result is to produce a data record, of high resolution both optically and over time, that reproduces in detail the process in the interesting region.

Advantageously, the scan region and/or individual scan parameters could be adapted at each scan, and in particular when scanning an interesting region at a higher resolution. An adaptation of the scan region could be accomplished in such a way that a region classified as interesting is further limited, and uninteresting regions still present are removed. The interesting region could thereby be even further reduced, and imaged at a higher optical resolution. Depending on the sample to be investigated, this could in fact be utilized in such a way that the sample is firstly divided into comparatively few scan fields, and is successively limited upon identification of an interesting region. For example, a sample could be divided into four square scan regions of identical size. If a region is classified as interesting, it could in turn be subdivided into four square regions of identical size. Another classification could be performed in the restricted regions. This procedure could be repeated until the interesting region is sufficiently delimited. The adaptation of scanning parameters could, for example, encompass modification of the illumination wavelength.

Classification of the scanned regions could be used for effective data reduction. For example, it is generally not sensible to store regions that have been classified as uninteresting. Such regions contain no events or objects of interest, and need not be subjected to subsequent detailed investigation by a specialist. Storage of the image data could thus usefully be limited to the regions of interest.

In the context of storage of the images generated by the microscope, they could firstly be deposited in a central mass memory. This requires that the unit that sends out the generated images have access to the mass memory. This unit will generally be the control computer. Another unit could, however, also be provided for appropriate processing of the images generated by the microscope, and for forwarding them to the mass memory. The microscope itself, or the scanner in the microscope, could also handle this task.

The mass memory thus serves initially as a buffer memory that allows the images to be exchanged with the further computers. The further computers would then access those data, carry out an analysis, and transmit the classification of the images. Only then are the images stored as interesting regions. Buffer storage, and storage of the interesting regions, can take place in the same mass memory. Also possible, however, is storage in different mass memories and/or on different computers.

Once a new image has been deposited in the mass memory, a message could be generated that signals the existence of a new image. The message could be received by at least one of the further computers. That further computer could then request transmission to it of the new image, and could carry out an analysis of the image after it is received. The microscope and/or the control computer could additionally generate further status information and transmit it via the network.

In order to arrive at a universal system into which the widest possible variety of computers can be linked, a protocol could be used for the transmission of messages, queries, control commands, data, and/or the like. Those protocols that additionally are platform-independent, i.e. that do not depend on the use of a specific operating system or computer, will be especially suitable. Because the microscopy system is intended to incorporate computers that are members of an existing network infrastructure, a protocol will be usable in particularly simple fashion if protocol messages can be transmitted without difficulty via the network. Protocols whose messages are, for example, filtered out by firewalls tend to be less suitable. Protocol messages that are converted into a text message have proven advantageous. The text message used is, by preference, an ASCII-coded text, although the text could also be coded in a different fashion. To enhance security in terms of manipulation or the unauthorized insertion of messages, the text messages could additionally be signed, encrypted, and equipped with further information. A very wide variety of signing and encryption methods known from practical use are available for this purpose. The text messages could then, in unencrypted or encrypted form, be embedded into network packets (e.g. TCP and/or UDP packets) and transmitted over the network via ports that are commonly used in other applications. If the protocol messages do not contain executable code, security is not thereby impaired.

Although the transmission of protocol messages in the form of a text message has proven to be particularly simple, other protocols and other ways of transmitting messages can nevertheless also be used. The use of the Distributed Communication Object Model (DCOM) or Simple Object Access Protocol (SOAP) may be used by way of example.

A wide variety of instructions from a further computer to other computers could be transmitted using the protocol messages. For example, once analysis and classification of an image have been performed, a further computer could generate and transmit to the mass memory an instruction to store or discard a specific image. An instruction directed to the control computer could contain information for controlling the microscope or the scanning operation. This could encompass, for example, selection of a specific region of the sample, an objective change, or refocusing of the objective.

In the method according to an embodiment of the present invention, multiple computers can analyze images substantially simultaneously. This could encompass, on the one hand, analysis of the same image using various criteria. Images obtained in chronological succession or at different locations in the sample could, however, also be analyzed in parallel fashion by different computers. Because instructions to the control computer may result from an analysis, in some circumstances multiple instructions from different computers will arrive simultaneously at the control computer. In that case the computers' instructions might collide. For example, one of the further computers might request the control computer to scan an interesting region in detail, while another of the further computers stipulates another region of the sample for further observation. In such cases a processing sequence or some other kind of conflict resolution is preferable. Care is preferably taken in this context that the integrity of the microscope system is maintained, and that no states occur that endanger the microscope. A supervisory unit, which monitors system integrity and thus allows the scanning operation to proceed without oversight, can be provided for this purpose.

Automatic documentation of the individual steps could be carried out in order to reconstruct individual operations during a scanning operation. XML databases could, for example, be set up and used for this purpose. This ensures that the scanning operation sequence can easily be reconstructed.

Advantageously, the method and the microscopy system according to an embodiment of the present invention can be used in a flexible and universal fashion. As a result, a wide spectrum of application areas can be covered, and a great variety of demands on the observation or analysis operation can be optimally reacted to. In particular, systems capable of running independently (e.g. the microscope with an associated control computer) can be integrated. The number and variety of integrated devices and systems is, however, also not limited. For example, further microscopes having an associated control computer, and an almost arbitrary number of further computers, can be integrated into the system. In addition, actuators or manipulators could be incorporated into the system. With these, for example, a medication could be applied onto the sample or the sample could be irradiated with a laser. Sensors, too, could be added to the overall logical system. With these, for example, the temperature of the sample or other parameters of interest could be sensed. Devices can also be attached to a computer and can create, through it, a connection to a network. Advantageously, an adaptation of the overall system can take place dynamically and/or during a scanning operation. Because devices or computers are incorporated in a software-based manner, these adaptations can be carried out by the user of the system him- or herself. In particular, there is no need for a service technician of the system manufacturer to be present and make the adaptations.

The present invention can furthermore be used in conjunction with a very wide variety of architectures and systems. For example, a wide variety of microscopes can be utilized. A transmitted-light microscope is usable in just the same way as a confocal microscope. Lastly, the kind of microscope that generates the image data is not critical. In principle, microscopes of different kinds can even be integrated into one overall system.

There is also no need to apply additional restrictions in terms of computer architectures. The further computers can thus encompass personal computers (PCs), Macintoshes, graphic workstations, personal digital assistants (PDAs), mobile telephones, and much more. There are also no limitations whatsoever in terms of the operating systems on the further computers. The use of Windows, Mac OS, BeOS, Linux, Unix, and Windows Mobile may be mentioned merely by way of example. These lists can, in principle, be extended indefinitely. Communication between the individual computers should be possible, and the data exchanged should be processable by the individual computers. This can be achieved, however, by using a simple and multi-platform protocol for intercommunication between the individual units of the microscopy system, and by converting the transmitted images into a reusable graphic format.

The analysis programs on the further computers, or the control programs on control computers, can furthermore be implemented any number of different ways, and can handle a wide variety of tasks. For example, a great variety of programming languages can be used. Merely by way of example and with no limitation thereto, an implementation using C++, C#, Java, Python, or Visual Basic may be mentioned. The individual applications can perform an analysis of the image data, generate 3-D images and 3-D models, assemble movies from individual images, handle regulation tasks, or display and process image data for a user. This list, too, can be modified and expanded as desired depending on the application. Existing analysis, control, evaluation, or display programs are thus also usable.

The network used for intercommunication and data exchange can likewise be constructed in a wide variety of ways. Merely by way of example and with no limitation thereto, the use of Ethernet, wireless local area network (WLAN), Universal Mobile Telecommunications System (UMTS), token ring, telephone modems, or digital subscriber line (DSL) may be mentioned. The network can also combine different network technologies. In one system, for example, computers may be connected via a cable-based Ethernet network. Individual computers are linked to them via a gigabit Ethernet using glass fibers, and individual mobile devices are incorporated via a WLAN.

Because existing hardware can be integrated to a large degree in the context of the method and the microscopy system according to the present invention, costs for the acquisition of high-performance computers can be considerably reduced. It is nevertheless possible to carry out a scanning operation that enables a high data throughput and supplies a great deal of interesting data about, and images of, a sample.

FIG. 1 schematically depicts an embodiment of a microscopy system according to the present invention. The microscopy system includes three microscopes 1.1, 1.2, and 1.3, each having a control computer 2.1, 2.2, and 2.3 associated with it. Microscopes 1 and control computers 2 are respectively interconnected via a communications connection 3 that can be constituted by a wide variety of interfaces known from practical use. Control computers 2 are connected via network connections 4 to a network server 5, to two network-attached storage (NAS) servers 6.1 and 6.2, and to further computers 7.1, 7.2, 7.3, and 7.4.

The network connections can be implemented in any number of different ways. The connections between control computers 2 and network server 5 are usefully realized using a high-performance network. Gigabit Ethernet could, for example, be used here. The connection between network server 5 and the NAS servers should also be dimensioned sufficiently to avoid data transfer bottlenecks that might otherwise possibly occur. Here as well, gigabit Ethernet would be one possible implementation of network connection 4. A slower standard connection, however, for example an Ethernet having a transfer rate of 100 Mbit, is generally sufficient for connecting network server 5 to further computers 7. Network connection 4 between network server 5 and further computers 7 can, however, also be implemented by way of a wireless network. The connection between further computer 7.4 (a PDA in FIG. 1) and network server 5 could be made, for example, via WLAN. The network structure can furthermore be differently constructed. In particular when the number of further computers 7 is large, for example, the connection to network server 5 can be constituted by switches, converters, or the like.

When the microscopy system according to an embodiment of the present invention is in operation, microscope 1 scans a sample and thereby generates a digital image. The image data are transmitted via communications connection 3 to control computers 2, and if applicable is post-processed by them by image processing. This could involve suppression of image noise or compensation for measurement optics distortions. The image data are then transmitted by control computers 2 to network servers 5. Alternatively, the scanner of microscope 1 could also send the image data directly to network server 5. Simultaneously or at least almost simultaneously with the transmission of image data to network server 5, status information could be generated that is transmitted to all or some of further computers 7.

When network server 5 receives new image data, it can in principle handle it in different ways. For example, the network server can first store the image data locally and transmit the data for storage to one of NAS servers 6 after classification has been performed by a further computer 7. Alternatively, the image can be transmitted directly to one of NAS servers 6 and then deleted, if necessary, once classification has been performed by one of further computers 7. The particular application instance will govern the decision as to a concrete embodiment of this storage operation.

Upon reception of a status information item, from one of microscopes 1 or from one of control computers 2, that new image data are available, one of further computers 7 can be caused to load the newly deposited image data. The status information of further information items can also be added. In addition, in particular in the case of an automated microscopy operation, a further computer 7 could be designated to handle analysis of the image data. Methods for capacity utilization control known from practical use can be used for this.

Once the image data have been loaded by one of the further computers, manual or automatic observation and/or analysis of the image data could occur. A manual analysis is useful when the quality of the image data obtained is not sufficient to guarantee an automatic analysis. In this case, interesting regions can often still be detected by a trained viewer. More usefully, however, an automatic analysis of the image data is carried out. In this, specific events or objects can be searched for and the associated regions can be classified as interesting.

As an alternative to a manual or automatic analysis, a combination of automatic and manual analysis can be used. For example, the image data could first be classified automatically into interesting and uninteresting regions. Regions that cannot be categorized as interesting or uninteresting could be presented to a specialist at one of further computers 7. He or she could manually classify the regions that cannot be classified, or set them aside for more detailed investigation and assessment later.

Once the image data have been analyzed by one of further computers 7, that computer generates an instruction to network server 5 indicating that the image data are to be stored or can be discarded. Alternatively, this instruction can also be sent directly to one of the NAS servers that is already storing the corresponding image data. On the other hand, an instruction could be given to the control computer, thereby influencing the scanning operation.

Further computers 7 can also encompass computers that do not perform an analysis of image data. PDA 7.4, for example, is connected to network server 5 but generally does not possess sufficient system resources to analyze image data. PDA 7.4 can, however, be used by a specialist to observe the scanning operation and to look through the images obtained. PDA 7.4 could also be used for manual post-classification in cases where an automatic classification of the image data was not possible. In this case the image is simply transmitted to the user, and the he or she issues an evaluation of the images. The demands on the hardware in this context are not very great.

A simple protocol is used to transmit messages, queries, control commands, and/or data between individual computers 2, 5, 6, and 7. A protocol message is converted into an ASCII text for this purpose. As a result, the protocol messages can be exchanged in platform-independent fashion between the individual computers via existing channels that, in some circumstances, are protected by a firewall.

Figure 2:
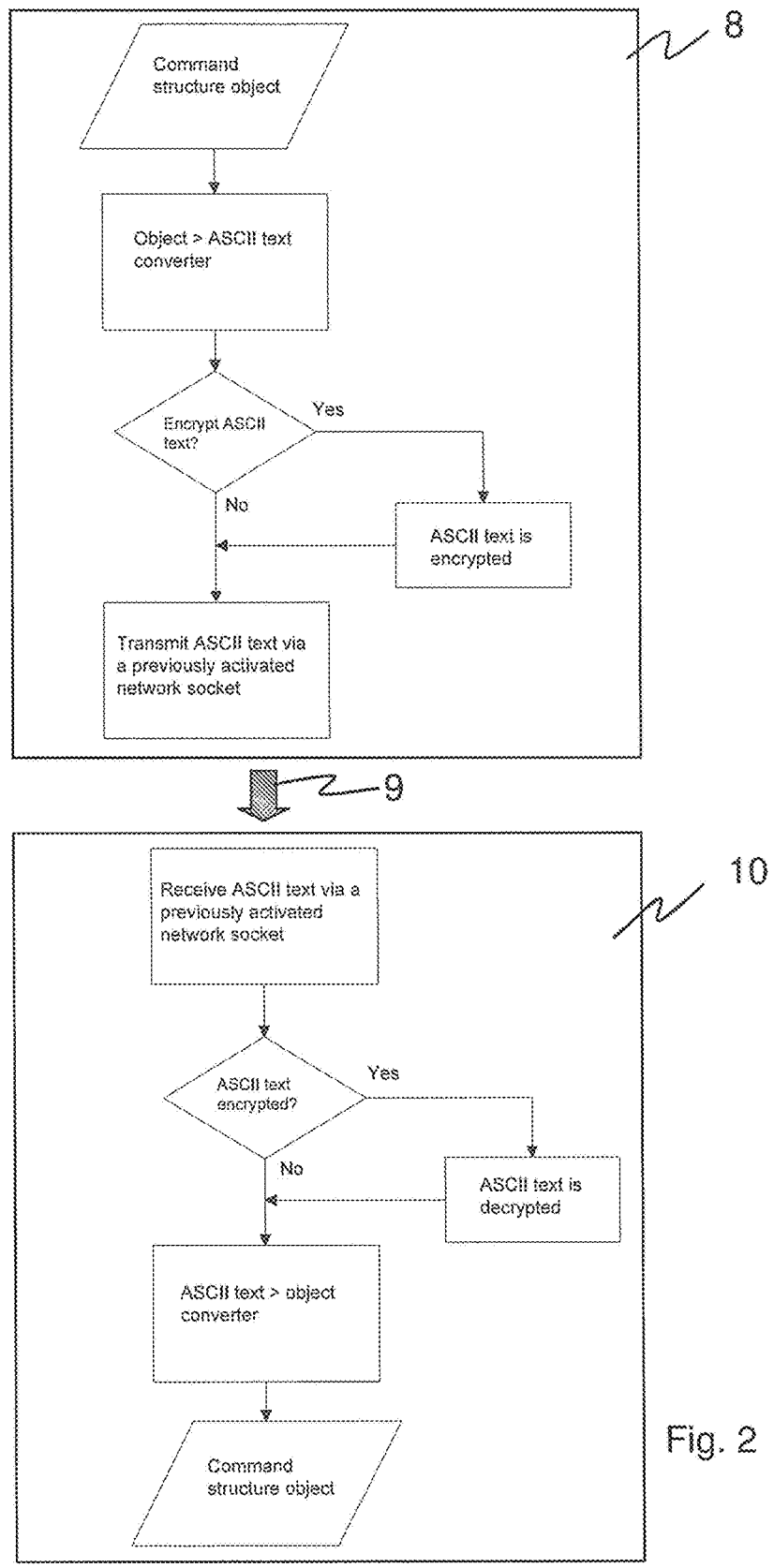
FIG. 2 is a block diagram showing conversion of an instruction into an ASCII text and vice versa.

FIG. 2 is a block diagram for conversion of a command structure object into an ASCII text and vice versa. A transmitter 8 of a protocol message firstly converts a command structure object into an ASCII string. In principle, a wide variety of allocations between the command structure object and an ASCII string can be selected for this.

After conversion of the command structure object into an ASCII text, a decision is made as to whether the text is to be encrypted before transfer. If encryption is selected, the ASCII text can be encrypted with any number of different encryption algorithms known from practical use. Selection of the encryption algorithm will be based on the particular security requirements.

The encrypted or unencrypted ASCII text is then transmitted via a previously activated network socket 9 to a receiver 10 of the protocol message. At receiver 10, the ASCII text is received via a previously activated network socket 9. The latter will generally be similar to the network socket of the transmitter. After reception of the ASCII text, a decision is made as to whether the ASCII text needs to be decrypted. In the case of an encrypted ASCII text, it is decrypted in a subsequent step. The ASCII text, now in decrypted form, is then converted by a converter back into a corresponding command structure object, which can now be processed by the receiver. This type of transfer is usable for any kind of protocol message and for any transmitter 8 and receiver 10.

Figure 3:
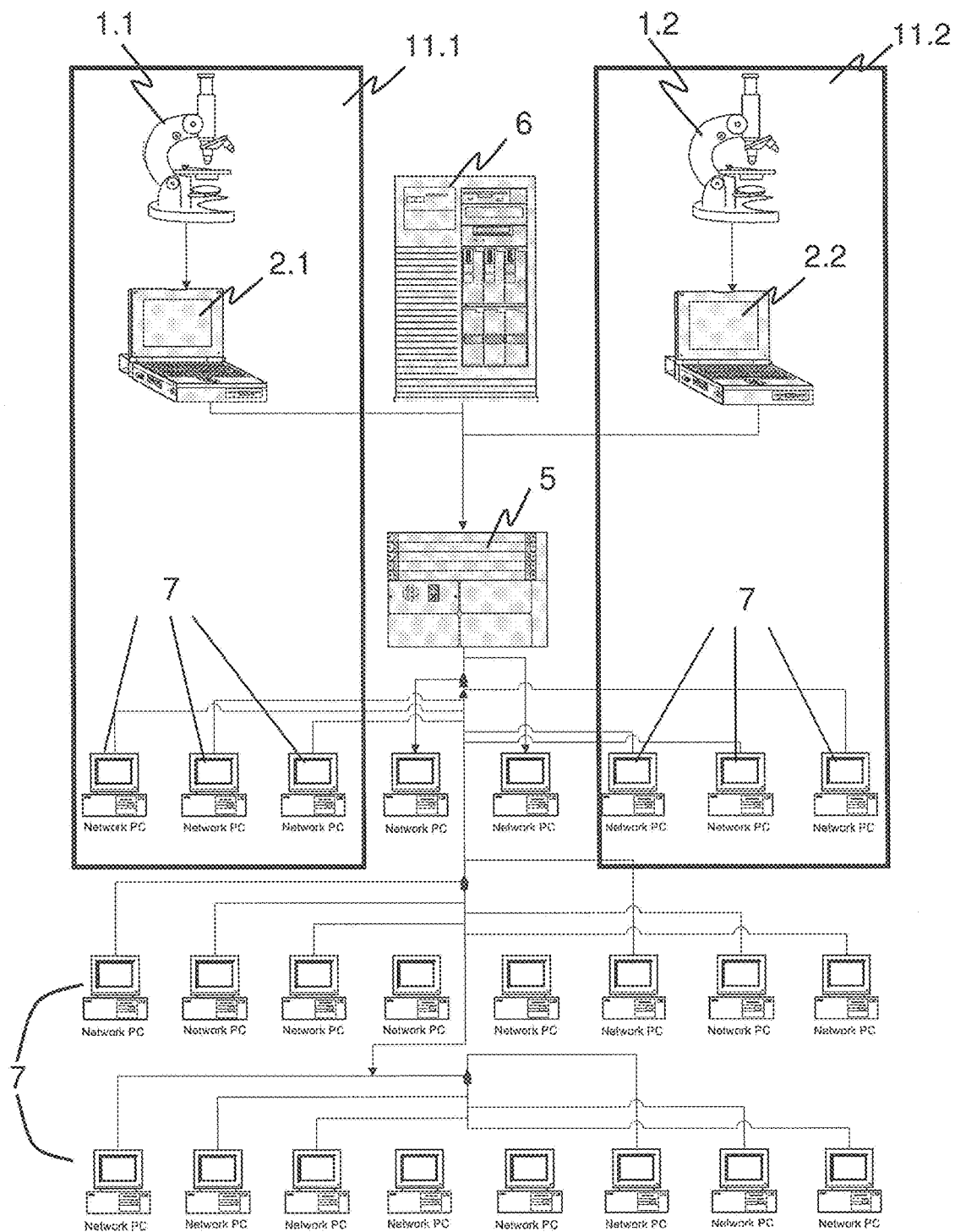
FIG. 3 schematically depicts a microscopy system according to an embodiment of the present invention having two subsystems.

FIG. 3 shows another configuration of the microscopy system according to an embodiment of the present invention. Two subsystems 11.1 and 11.2 are embodied in the microscopy system. Each subsystem 11 contains a microscope 1 and an associated control computer 2. Additionally integrated into each of subsystems 11 are three network PCs constituting further computers 7. Both subsystems 11 access a network server 5 and an NAS server 6. All the computers are interconnected by a network. The network includes, in addition to computers 7 of subsystems 11, further computers 7 that, however, are not used for the analysis, observation, or processing of image data and are not at present incorporated into the microscopy system. Each subsystem thus represents a subset of a larger network having many further computers 7. As necessary and possible, further computers 7 can be switched into or disconnected from each subsystem 11. Because these operations occur merely as logical operations, no restructuring of a network is necessary, so that a subsystem 11 can be enlarged or reduced dynamically and during the runtime of a scanning operation. In the embodiment according to FIG. 3, the two subsystems are separate from one another. Other configurations could, however, also comprise overlapping subsystems. A microscope used in shared fashion could be encompassed, for example, or individual further computers could be incorporated into both subsystems.

Figure 4:
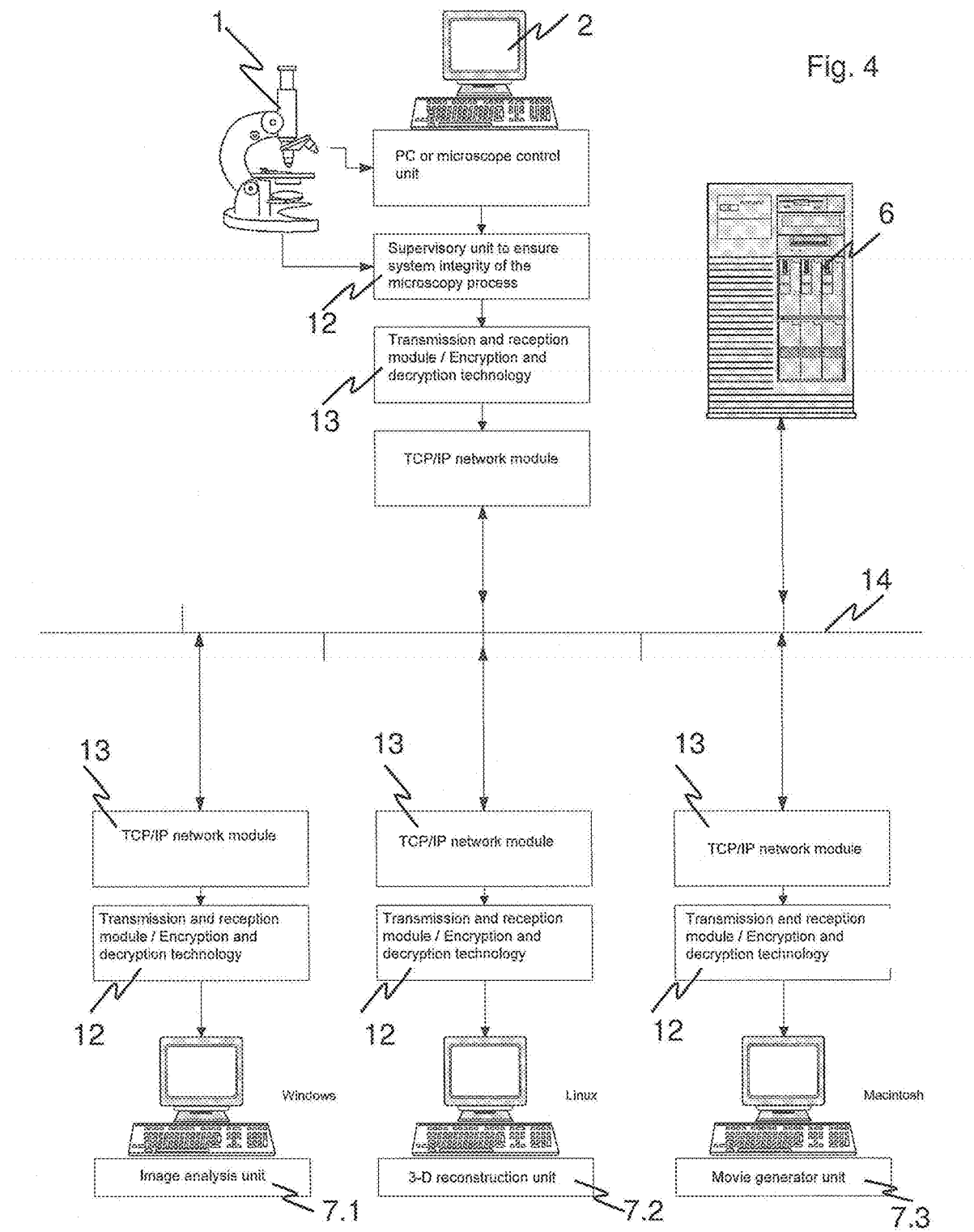
FIG. 4 is a block diagram showing a microscopy system according to an embodiment of the present invention having a supervisory unit.

FIG. 4 is a block diagram of a microscopy system according to the present invention, elucidating another aspect. Once again, a microscope 1 is connected to a control computer 2. Additionally provided is a supervisory unit 12 that is intended to ensure system integrity. The purpose is to guarantee that a scanning operation always proceeds in such a way that the microscope and other system components are not damaged during the scanning operation. Supervisory unit 12 continuously checks whether incoming instructions can be executed, or whether their execution at the present time is not appropriate or would in fact result in damage to the microscope. For example, an autofocus instruction is not advisable just when an objective change is being carried out. The supervisory module would then postpone the autofocus instruction until the objective change has been carried out, and perform the autofocus action only thereafter. Likewise, it makes little sense to terminate a scanning operation if it has not yet proceeded to completion or if the data have not been completely stored. In this case the supervisory module would firstly complete the entire scanning operation or storage action, and only then implement the instruction. Another task of the supervisory unit could be to carry out a movement of the microscope stage only when there is assurance that no other parts, for example an objective or a manipulator, are present in the movement region of the stage.

Supervisory unit 12 is further connected to a transmission and reception module that handles the conversion of messages, status reports, instructions, or the like into a suitable protocol. Encryption and decryption units can furthermore be integrated into this module. The transmission and reception module is connected to a network module that permits data exchange via an Ethernet connection 14.

An NAS server 6 and three further computers 7 can be addressed via this Ethernet connection 14. Each of the further computers possesses a network module that is connected to a transmission and reception module 12. Data can thereby be exchanged between the individual computers 2, 6, and 7.

Each of further computers 7 can handle a specific task and can be implemented using different hardware and software. Further computer 7.1, for example, encompasses a PC that is operated under the Windows operating system. This computer 7.1 handles image analysis of the images generated by the microscope. Another computer 7.2, operated under the Linux operating system, handles 3-D reconstruction of the image data stored on NAS server 6. Computer 7.3 is a Macintosh that creates a time correlation among various image data stored on NAS server 6 and generates a movie from them, allowing the visualization of processes over time in the sample scanned by microscope 1.

The configuration of the system according to an embodiment of the present invention of FIG. 4 shows that multiple processes proceeding almost independently of one another are proceeding concurrently. The microscope can continuously scan the sample and store the images obtained, via the control computer or directly, on a central mass memory in the form of NAS server 6. More or less independently thereof, a further computer analyzes the data obtained, classifies individual regions, and optionally intervenes in the execution of the scanning operation. Further computers can then handle image processing in order to generate a 3-D model or a movie. FIG. 4 also shows how easily further systems can be linked into the microscopy system. For example, a further control computer that, for example, activates a manipulator could easily be linked into Ethernet connection 14. In this case an additional communications connection could be created with control computer 2, to ensure that system integrity is maintained. Sensors could furthermore be coupled to Ethernet connection 14, and data (for example ambient temperature, relative humidity, or the intensity of the light irradiated onto the sample) could be transmitted to individual computers of the system.

Figure 5:
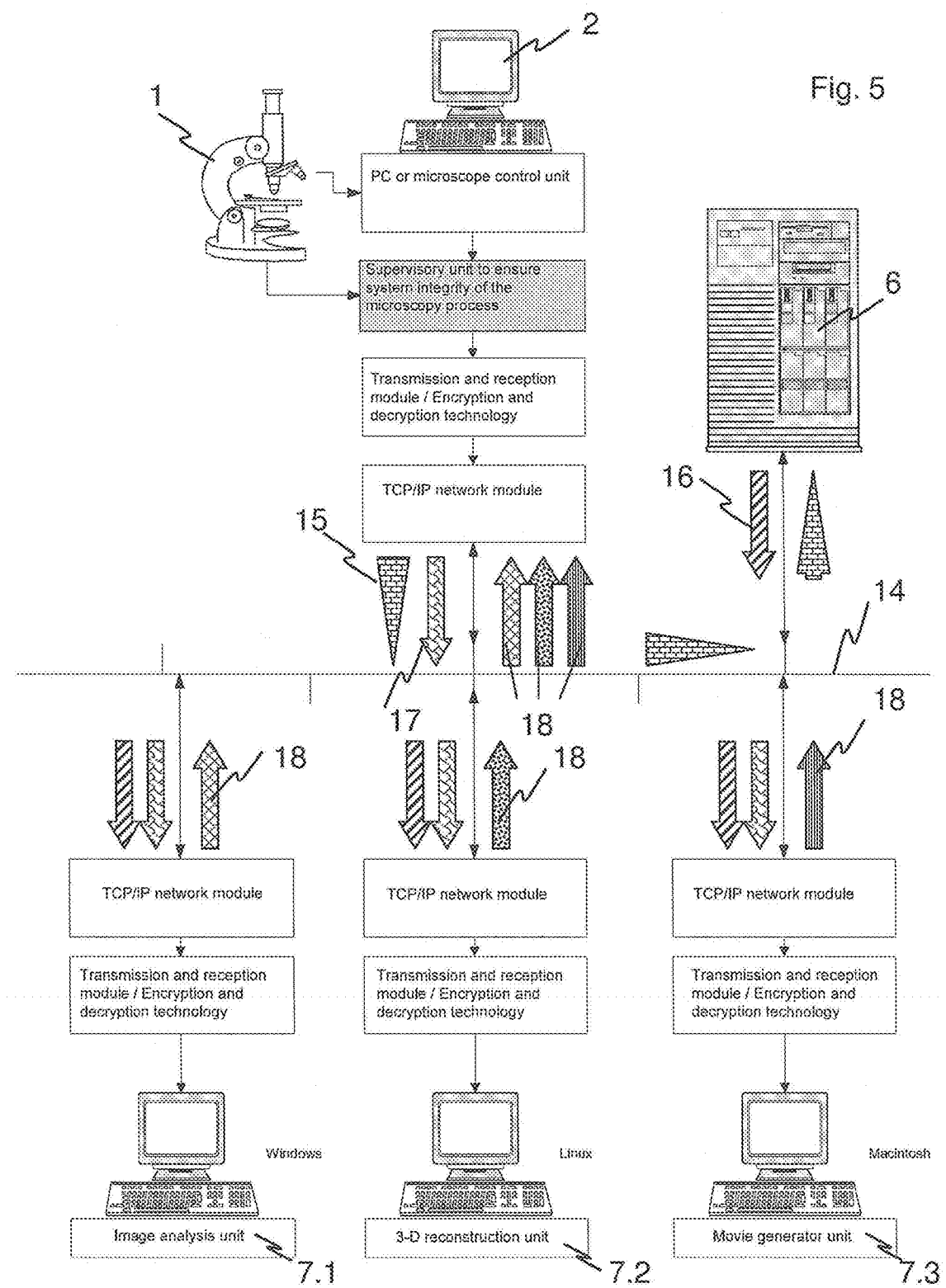
FIG. 5 is a block diagram showing the microscopy system as shown in FIG. 4 including individual signal flows.

FIG. 5 once again shows the system as shown in FIG. 4, but additionally depicts individual communication flows in the system. Each data flow is illustrated using a differently configured arrow. Image data 15 generated by the microscope are transmitted via network connection 14 to NAS server 6, and stored there in a mass memory. These image data can be requested in turn by other computers and downloaded onto a further computer 7. These data flows are depicted with arrow 16.

Control computer 2 can generate control signals 17 in addition to image data and thereby, for example, inform further computers 7 of the existence of new image data. Each of further computers 7 can transmit instructions to microscope 1 or to control computer 2 by way of control signals 18, and thereby influence the scanning operation.

Figure 6:
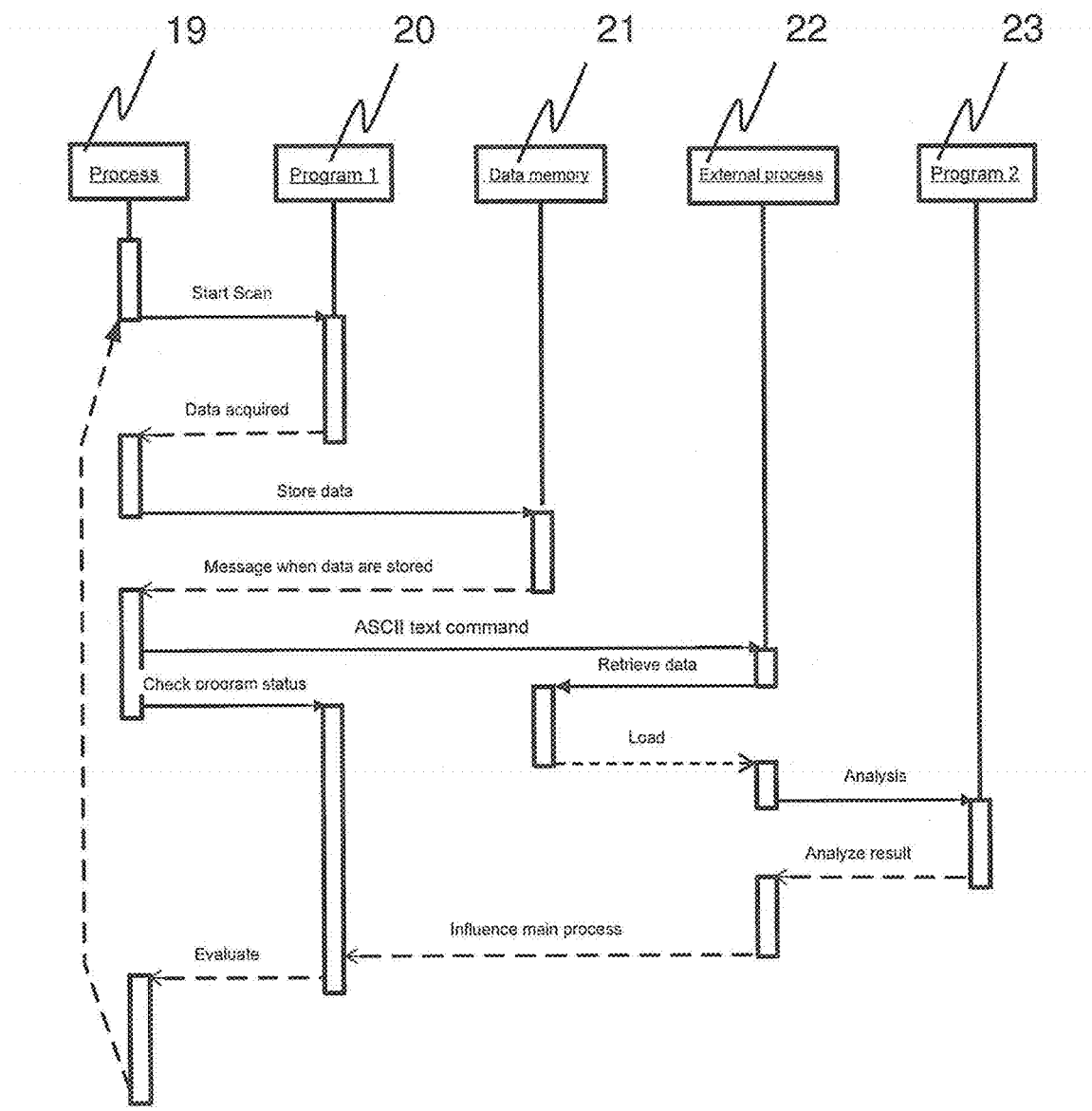
FIG. 6 is a sequence diagram showing an execution sequence in accordance with a method according to an embodiment of the present invention.

FIG. 6 illustrates individual signal flows in the context of data recovery and analysis. In the sequence diagram, the first lifeline designates the main process on the control computer. The latter starts a program that is represented by the second lifeline. The third line represents activity on the computer for storing the image information, which in the embodiments so far is NAS server 6. The fourth lifeline illustrates the main process on a further computer 7, and the last vertical line is the activity of a program that is started on further computer 7.

In main process 19, firstly the main process is initialized and then program 20 is started with the call "Start Scan." A scanning operation is then initiated by program 20, and is controlled by it. As soon as the image data are acquired, program 20 terminates and gives the acquired image data back to main process 19. In main process 19, the data are then processed and prepared for storage; and the data are then, with the call "Store Data," transferred to the mass memory that saves the data in suitable fashion in process 21. As soon as the data have been successfully stored, activity is terminated and a message is sent back to the control computer. In main process 22, a protocol message in the form of an ASCII text is then generated and is transferred to main process 22 of a further computer. This protocol message causes the further computer to analyze the image data that have just been generated. The further computer does so by receiving the protocol message and downloading the image data from the mass memory. The call "Retrieve Data" is sent to data memory 21 for this purpose. The latter gives the data loaded from mass memory back to main process 22 on the further computer. In main process 22, an analysis is then started with program 23; and once analysis has been performed, the result is given back to main process 22. From these results, main process 22 generates instructions that are intended to influence main process 19 on the control computer. These instructions are given back to program 20 on control computer 2.

After initiation of the analysis process on the further computer by main process 19, a process 20 is started (by main process 19, in order to avoid any blockage of the control computer) that checks at regular intervals whether analysis of the most recently obtained data is already complete. During this time, the control computer is in principle ready for further activities. In the example depicted in FIG. 6, however, a execution waits until analysis of the data on the further computer is complete, and only then branches back to the beginning of main process 19. Alternatively, however, that branching could already occur earlier, even before the analysis results from the further computer are available. In this case the program status check in program flow 20 simply needs to be outsourced to a further process, so that program process 20 is not blocked by the program status check.

As soon as program 20 receives the protocol message with the instructions from the further computer, it terminates and gives back to main process 19 of the control computer the information and instructions that it has received. Main process 19 then starts, for example, a realignment of the microscope parameters, and at the same time carries out a system integrity check. Once the microscope has been realigned, the main process branches back to the beginning and starts a new scanning operation.

Figure 7:
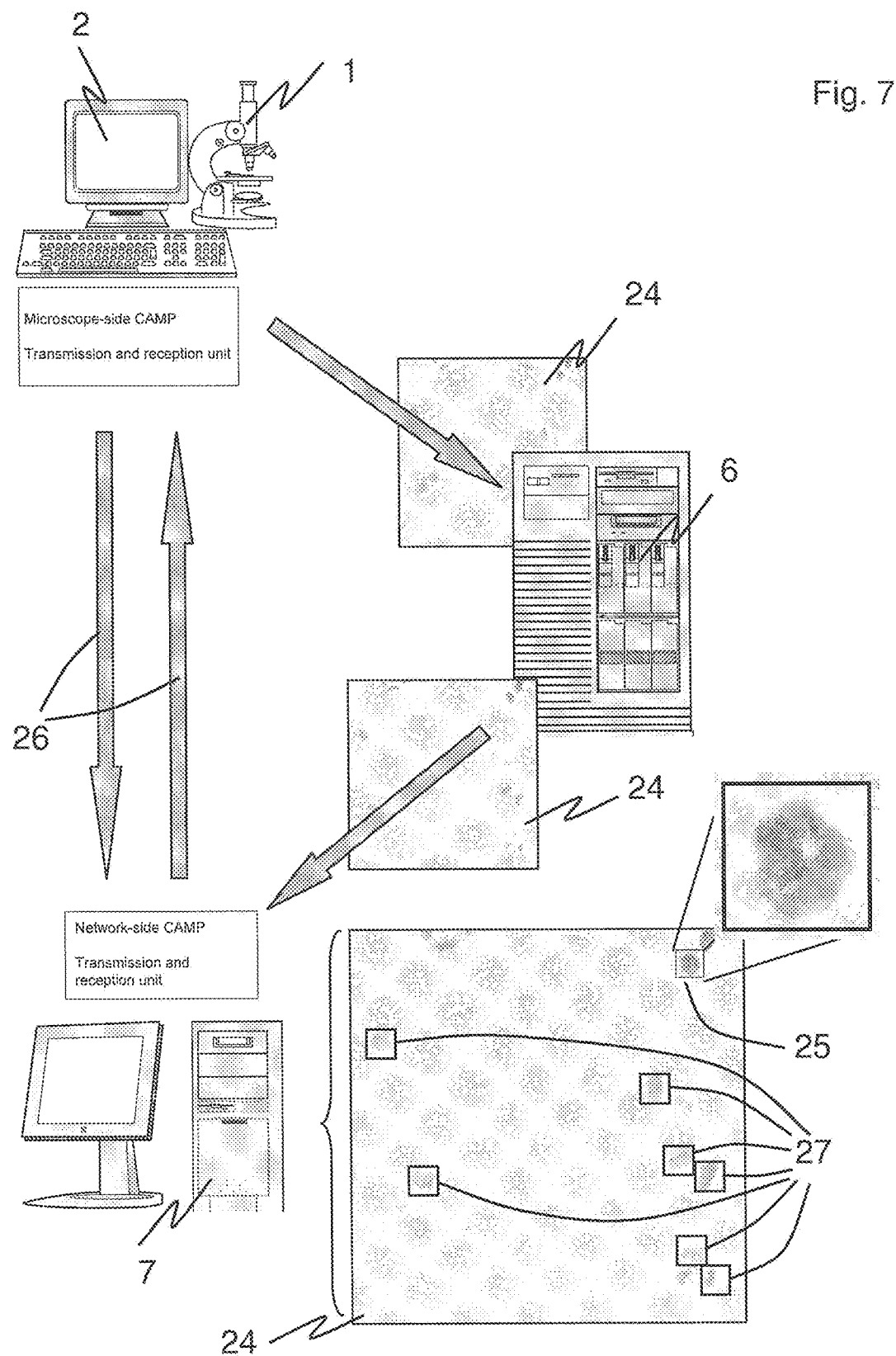
FIG. 7 schematically depicts a microscopy system according to an embodiment of the present invention for discovering rare and unexpected events.

FIG. 7 shows, once again schematically, the general sequence of a scanning operation. For the sake of simplicity, only one microscope having a control computer 2, one NAS server, and one further computer 7 are depicted in the Figure. Image data 24 generated by the interaction of microscope 1 and control computer 2 are transferred to NAS server 6, where they are stored. Image data 24 represent in this case a larger field of the sample, imaged at low resolution. This field could in fact encompass the entire sample. Image data 24 are transferred for analysis to further computer 7, where the individual regions are classified. In the exemplifying embodiment depicted in FIG. 7, an interesting region 25 is found in image data 24. Instructions, control commands, messages, status reports, and the like are exchanged by intercommunications 26 between control computer 2 and further computer 7. After interesting region 25 has been detected, further computer 7 generates a control command that is sent via intercommunication 26 to control computer 2. As a result, control computer stops the current scanning operation, switches from the low-resolution objective to a higher-resolution objective, displaces the microscope stage as applicable to the position at which the interesting region was detected, in some circumstances carries out an autofocus operation, and scans the interesting region in more detail. It would also be possible in this context to carry out a 3-D scan over a certain time period, in which the interesting region is scanned repeatedly in different scan layers. After the scanning time has elapsed, the control computer switches the microscope back to the low-resolution objective and once again scans the larger field, or the entire sample, for interesting regions.

In addition to the interesting region having a rare event (region 25), a number of further possibly interesting regions 27 are also contained in image data 24. These image regions 27 cannot, however, be divided by automatic classification into interesting or uninteresting regions. Different procedures could be used here. On the one hand, the regions could all be presented to a specialist for assessment. On the other hand, these regions could be conveyed to another classifier that further investigates the possibility that the regions merely represent uninteresting events or objects. The number of regions 27 can thereby be reduced further. Those regions 27 that cannot be categorized as interesting or uninteresting could then be presented to a specialist so that he or she can make a conclusive classification of the regions. These regions might on the one hand encompass cells that were not scanned clearly, but on the other hand an unexpected event may also have been imaged. Because it will generally be difficult to generate a classifier for unexpected events, inspection by a specialist is often the only option for classification.

In conclusion, be it noted very particularly that the exemplifying embodiments, selected in entirely arbitrary fashion above, serve merely for discussion, but do not limit it to the exemplifying embodiments.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

PARTS LIST

1 Microscope
2 Control computer
3 Communications connection
4 Network connections
5 Network server
6 NAS server
7 Further computers
8 Transmitter (of a protocol message)
9 Network socket
10 Receiver (of the protocol message)
11 Subsystem
12 Supervisory unit
13 Transmission and reception module
14 Ethernet connection
15 Image data
16 Downloaded image data
17 Control data (from control computer)
18 Control data (to control computer)
19 Main process (control computer)
20 Program (on control computer)
21 Data memory
22 Main process (on further computer)
23 Program (on further computer)
24 Image data
25 Interesting region
26 Intercommunication
27 Possibly interesting regions

What is claimed is:

1. A method for scanning a sample using an electrically or electronically controllable microscope, comprising the steps of:
   dividing the sample into a plurality of scan fields;
   performing a scanning of the sample so as to generate a plurality of images of the sample in the scan fields, the plurality of images being generated at different times and/or different locations of the sample, the microscope being controlled via a control computer during the scanning;
   observing and/or analyzing the generated images using at least one further computer connected via a network so as to identify interesting regions of the sample; and
   successively limiting the scan fields of the sample based on the identifications of interesting regions.

2. The method according to claim 1, wherein the observing and/or analyzing of yields a classification into the interesting regions and uninteresting regions, and wherein the classification is accomplished by allocating specific geometric properties to interesting objects in the sample.

3. The method according to claim 1, wherein at least one of the further computers supervises the scanning operation.

4. The method according to claim 1, wherein an adaptation of the scan fields is accomplished in such a way that at least one of the interesting regions is further limited and uninteresting regions still present are removed.

5. The method according to claim 1, further comprising modifying an illumination wavelength based on the observing and/or analyzing.

6. The method according to claim 1, wherein storage of the image data is limited to the interesting regions.

7. The method according to claim 1, wherein an object is classified as an unexpected event based on a determination that the object cannot be unequivocally classified as an interesting or uninteresting object.

8. The method according to claim 7, wherein the object classified as the unexpected event is presented to an operator.

9. The method according to claim 1, wherein the scanning of the sample is performed continuously and wherein regions that do not change during the continuous scanning are classified as uninteresting.

10. The method according to claim 1, wherein the scanning is continued during the observing and/or analyzing of the generated images.

11. The method according to claim 1, wherein the generated images obtained in chronological succession or at the different locations of the sample are analyzed in parallel fashion by different computers.

12. The method according to claim 1, wherein the control computer is connected to at least one of personal digital assistants (PDAs) and mobile telephones via a network.

13. The method according to claim 1, wherein the observing and/or analyzing includes searching for specific events and classifying associated regions as the interesting regions.

14. A method for scanning a sample by means of an electrically or electronically controllable microscope, comprising the steps of:
performing a scanning of the sample so as to generate a plurality of images of the sample in the scan fields, the plurality of images being generated at different times and/or different locations of the sample, the microscope being controlled via a control computer during the scanning;
identifying, by a classifier, interesting regions within the generated images;
determining that a process is occurring in one of the interesting regions; and
continuously investigating, over a period of time, the region in which the process is determined to be occurring.

15. The method according to claim 14, wherein the identifying yields a classification into the interesting regions and uninteresting regions, and wherein the classification is accomplished by allocating specific geometric properties to interesting objects in the sample.

16. The method according to claim 14, wherein at least one of the further computers supervises the scanning operation.

17. The method according to claim 14, further comprising adapting a scan region of the scanning in such a way that at least one of the interesting regions is further limited and uninteresting regions still present are removed.

18. The method according to claim 14, further comprising modifying an illumination wavelength based on the identifying.

19. The method according to claim 14, wherein storage of the image data is limited to the interesting regions.

20. The method according to claim 14, wherein an object is classified as an unexpected event based on a determination that the object cannot be unequivocally classified as an interesting or uninteresting object.

21. The method according to claim 20, wherein the object classified as the unexpected event is presented to an operator.

22. The method according to claim 14, wherein the scanning of the sample is performed continuously and wherein regions that do not change during the continuous scanning are classified as uninteresting.

23. The method according to claim 14, wherein the scanning is continued during the identifying of the interesting regions.

24. The method according to claim 14, wherein the generated images obtained in chronological succession or at the different locations of the sample are analyzed in parallel fashion by different computers.

25. The method according to claim 14, wherein the control computer is connected to at least one of personal digital assistants (PDAs) and mobile telephones via a network.

26. The method according to claim 14, wherein the identifying includes searching for specific events and classifying associated regions as the interesting regions.

* * * * *